United States Patent [19]

Hubaud et al.

[11] Patent Number: 5,075,102
[45] Date of Patent: Dec. 24, 1991

[54] SUNTAN ACCELERATOR COMPOSITION

[75] Inventors: Jean-Claude Hubaud, Gap; Daniele Thiry, La Turbie, both of France

[73] Assignee: Lancaster Societe Anonyme Monegasque, Monaco

[21] Appl. No.: 478,148

[22] Filed: Jan. 25, 1990

[30] Foreign Application Priority Data

Jan. 27, 1989 [GB] United Kingdom ................ 8901837

[51] Int. Cl.$^5$ ...................... A61K 7/021; A61K 7/42; A61K 7/44; A61K 9/12
[52] U.S. Cl. .......................................... 424/59; 424/47; 424/60; 424/63; 514/844; 514/847; 514/938; 514/944
[58] Field of Search .................................... 424/59, 60

[56] References Cited

U.S. PATENT DOCUMENTS 2,418,695  4/1947  Brown ................................... 424/59
2,770,631 11/1956  Merker ............................. 424/59 X

OTHER PUBLICATIONS

Goodman, 1936, Cosmetic Dermatology, pp. 526 and 527.

Primary Examiner—Dale R. Ore
Attorney, Agent, or Firm—Rosenman & Colin

[57] ABSTRACT

A sun tan composition comprises a xanthine and a cosmetically acceptable copper salt in a compatible, cosmetically acceptable vehicle for accelerating the development of a sun tan and for protecting the skin.

5 Claims, No Drawings

SUNTAN ACCELERATOR COMPOSITION

The present invention relates to a sun tan product and in particular to compositions which will protect the skin and accelerate the development of a sun tan, processes for the preparation thereof and methods for using the same.

Sun tan products have been proposed, the primary function of which is to significantly reduce the amount of harmful ultra violet radiation falling on the skin, and thus prevent burning, whilst allowing through sufficient of the less harmful radiation to produce a tan (Harry's Cosmeticology, 7th edition, ed J. B. Wilkinson and R. J. Moore, George Goodwin, London, 1982, p 231). The problem however remains that the development of a sun tan requires prolonged exposure to the sun. Maximum pigmentation is believed to occur after 100 hours, but exposure needs to be progressive to avoid burning.

A sun tan is the consequence of the enhanced production of the pigment melanin in the epidermis, in response to exposure of the skin to ultra violet radiation, in a process referred to as melanogenesis. Tyrosine is converted, in a series of steps which are under enzymatic control, to melanin, a key enzyme being tyrosinase, a metallo-enzyme dependent upon copper. (G. Prota, Recent Advances in the Chemistry of Melanogensis in Mammals, *J. Invest. Dermatol.* 75(1), 122-7, 1980).

Products have already been proposed to accelerate the tanning process which contain tyrosine, to increase the substrate available for tyrosinase (M. Duggan et al, *Cosmetics* and *Toiletries*, 1987, 102, 97).

We have found that improved results can be obtained by an alternative approach, based upon a consideration of results derived from basic biochemical studies of cells.

The activity of the enzyme tyrosinase is found to be cyclic-AMP dependant, cyclic-AMP itself being inactivated by phosphodiesterase enzymes, of which xanthines such as caffeine and theophylline are inhibitors. In addition, silicon is known to act as an activator of cyclic-AMP, and inhibits lipoperoxidation (Charnot. *Ann Endocrinal Paris.* 1971, 32, 397).

Accordingly, the present invention provides a sun tan accelerator composition comprising a xanthine and a cosmetically acceptable copper salt in a compatible, cosmetically acceptable vehicle.

Suitable xanthines include caffeine and theophylline. Preferably the xanthine is theophylline.

The xanthine is typically present in the range 0.01 to 10%, preferably 0.1 to 5%, more preferably 0.2 to 1%, by weight of the composition.

Cosmetically acceptable copper salts include the gluconate. The copper salt is typically present in the range 0.0001 to 1%, preferably 0.001 to 0.1%, by weight of the composition.

In a preferred aspect, compositions of the invention may also include agents which protect the skin against the sun. For instance, the composition may include a compatible silicon-containing compound, preferably an organo-silicon compound, for instance monomethylsilanetriol lactate or other derivatives thereof, such as monomethylsilanetriol mannuronate, or silanolpyrrolidone sodium carboxylate, typically present in the range 0.0001 to 1%, preferably 0.001 to 0.1% by weight of the composition.

Optionally, the composition may include glycine or another amino acid, or a mixture of amino acids, which may be present in the range 0.001 to 5%, preferably 0.01 to 2% by weight of the composition.

The composition may also contain an ultra violet radiation filter which may be any one conventionally used in the art for such purposes, for instance octyl-dimethyl-paraaminobenzaldehyde, benzophenones, 2-phenylbenzimidazole-5-sulphonic acids, ethyldihydroxypropyl-paraaminobenzaldehyde, butylmethoxydibenzoylmethane or octylmethoxycinnamate.

The compositions of the invention are applied topically and may be presented in a wide variety of different forms suitable for such application, for instance, oils, creams, gels, aqueous or alcoholic lotions, aerosol sprays or any other cosmetic formulation conventionally used for sun tan products.

The major requirement of the carrier is that it is cosmetically acceptable and is compatible with the active ingredients of the composition i.e. the carrier does not inhibit the tan accelerator action.

The carrier may itself have some efficacy as a tan accelerator. Examples of suitable carriers include sodium stearate; glyceryl stearate and PEG-100 stearate; glycerylstearate/PEG-30 stearate; sorbitan monostearate, PEG-7 hydrogenated castor oil; beeswax and stearic acid/PEG-7 hydrogenated castor oil; methoxy PEG-22 dodecylgycol copolymer/PEG-45 dodecylglycolcopolymer/hydroxyoctacosanyl hydroxystearate; diethanolamine cetylphosphate/glycerylstearate; methylglucose sesquistearate/methylglucth-20 sesquistearate; and polyglycol-2-PEG-4 stearate/diethanolamine cetylphosphate.

Preferably the composition is in the form of an alcoholic lotion or an emulsion, which suitably is either an oil-in-water or water-in-oil emulsion.

In addition and if necessary, further additives conventionally used in cosmetics formulations, such as humectants, emollients, perfumes, dyes, preservatives, and viscosity modifiers, may be added.

The invention further provides a process for the preparation of compositions of the inventions, which process involves admixing of the ingredients in any suitable order and adjusting the pH to a pH in the range 5.0 to 7.0.

The invention also provides a method for accelerating the development of a sun tan and which may also protect the skin, which method comprises application to the skin of a composition according to the invention, prior to, and during exposure to, the sun or an artificial sun lamp. Repeated application may be necessary during prolonged exposure, to maintain efficacy.

The following Examples illustrate compositions of the invention.

EXAMPLES

EXAMPLE 1

Emulsion

|  | w/w % |
|---|---|
| Theophylline | 1.00 |
| Copper gluconate | 0.02 |
| Monomethylsilanetriol lactate | 0.50 |
| Sodium stearate | 0.10 |
| Mineral oil | 5.50 |
| Glyceryl stearate | 1.50 |
| Peg-75 lanolin-oil | 0.25 |
| Avocado oil | 0.10 |

-continued

| | w/w % |
|---|---|
| Preservative | 0.25 |
| Tocopheryl acetate | 0.05 |
| Glycine | 0.05 |
| Perfume | 0.30 |
| Water | qs |

EXAMPLE 2

Emulsion with ultra violet filter

As Example 1 plus octyldimethyl-paraaminobenzaldehyde at 3%.

EXAMPLE 3

Emulsion

| | w/w % |
|---|---|
| Glyceryl stearate and Peg 100 stearate | 5.00 |
| Cetyl alcohol | 2.50 |
| Sorbitan stearate | 0.30 |
| Mineral oil | 10.50 |
| Octyl palmitate | 9.00 |
| Preservative | 0.40 |
| Theophylline | 0.50 |
| Glycerine | 5.00 |
| Copper Gluconate | 0.20 |
| Monomethylsilanetriol lactate | 0.003 |
| Glycine | 0.05 |
| Perfume | 0.30 |
| Water | qs |

EXAMPLE 4

Emulsion

| | w/w % |
|---|---|
| Glyceryl stearate and PEG-30 stearate | 5.00 |
| Stearic acid | 5.00 |
| Petrolatum | 5.00 |
| Octylmethoxycinnamate | 2.50 |
| Octyldimethyl-paraaminobenzaldehyde | 1.50 |
| Theophylline | 0.50 |
| 2-Phenylbenzimidazole-5-sulphonic acid | 2.50 |
| Preservative | 0.20 |
| Copper gluconate | 0.01 |
| Glycine | 0.05 |
| Perfume | 0.35 |
| Silanol lactate | 0.50 |
| Water | qs |

EXAMPLE 5

Emulsion

| | % |
|---|---|
| Methoxy PEG-22 and dodecylglycolcopolymer | 5.00 |
| PEG-45 and dodecylglycolcopolymer | 4.00 |
| Hydroxyoctacosanyl hydroxystearate | 10.00 |
| Petrolatum | 30.00 |
| Octylmethoxycinnamate | 2.50 |
| Octyldimethyl-paraaminobenzaldehyde | 3.00 |
| Theophylline | 1.00 |
| Silanol lactate | 0.5 |
| Copper gluconate | 0.01 |
| Glycine | 0.05 |
| Preservative | 0.30 |
| Perfume | 0.60 |
| Water | qs |

EXAMPLE 6

Alcoholic solution

| | % |
|---|---|
| Denaturated alcohol | 78.00 |
| Octyldimethyl-paraaminobenzaldehyde | 5.00 |
| Octylmethoxycinnamate | 2.00 |
| Theophylline | 0.50 |
| Silanol lactate | 0.50 |
| Glycine | 0.05 |
| Copper gluconate | 0.01 |
| Perfume | 0.50 |
| Water | qs |

We claim:

1. A sun tan accelerator composition comprising frm 0.01 to 10% by weight of the composition of a xanthine selected from the group consisting of caffeine and theophylline, and from 0.0001 to 1% by weight of the composition of copper gluconate in a compatible, cosmetically acceptable vehicle.

2. A composition according to claim 1, which includes monomethylsilanetriol lactate present in the range of from 0.0001 to 1% by weight of the composition.

3. A composition according to claim 1, in the form of an alcoholic lotion or emulsion.

4. A process for the preparation of sun tan accelerator composition as claimed in claim 1, comprising admixing the ingredients in any suitable order.

5. A method for accelerating the development of a sun tan, which method comprises application to the skin of a composition as claimed in claim 1, prior to, and/or during exposure to, the sun or an artificial sun lamp.

* * * * *